US006835711B2

(12) United States Patent
Eisenbach-Schwartz et al.

(10) Patent No.: US 6,835,711 B2
(45) Date of Patent: Dec. 28, 2004

(54) USE OF POLY-GLU,TYR FOR NEUROPROTECTIVE THERAPY

(75) Inventors: Michal Eisenbach-Schwartz, Rehovot (IL); Ester Yoles, Nahal Sorek (IL); Ehud Hauben, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/893,344

(22) Filed: Jun. 28, 2001

(65) Prior Publication Data

US 2003/0003082 A1 Jan. 2, 2003

(51) Int. Cl.[7] ............................................... A61K 38/00
(52) U.S. Cl. ............................................. 514/2; 514/12
(58) Field of Search ................................. 435/325, 363, 435/366, 372, 372.3, 7.1, 32, 69.1; 514/2, 12, 21; 530/324, 350, 300

(56) References Cited

FOREIGN PATENT DOCUMENTS

WO WO 99/34827 A1 7/1999

OTHER PUBLICATIONS

Cady et al. (2000) Response of Murine gamma–delta T Cells to the Synthetic Polypeptide Poly–Glu50–Tyr50. The Journal of Immunology 165:1790–1798.*
Fisher et al. (Jan. 1, 2001) Vaccination for Neuroprotection in the Mouse Optic Nerve: Implications for Optic Neuropathies. The Journal of Neuroscience 21(1): 136–142.*
Schori et al. (Mar. 13, 2001) Vaccination for protection of retinal ganglion cells against death from glutamate cytotoxicity and ocular hypertension: Implications for glaucoma. PNAS 98(6): 3398–3403.*
Sucher et al. (1997) Molecular Basis of Glutamate Toxicity in Retinal Ganglion Cells. Vision Res. 37(24): 3483–3493.*
Schori et al. (2001) T–cell based immunity counteracts the potential toxicity of glutamate in the central nervous system. Journal of Neuroimmunology. 119(2): 199–204.*

Vidovic et al. (1985) Recessive T Cell Response to Poly(Glu50Tyr50) possibly caused by self tolerance. The Journal of Immunology. 134(6): 3563–3568.*
Stedman's Medical Dictionary (2002) Physicians' Desk Reference, Medical Economics Company Inc.*
Hauben et al. (Sep. 1, 2000) "Passive or Active Immunization with Myelin Basic Protein Promotes Recovery from Spinal Cord Contusion." The Journal of Neuroscience 20(17): 6421–6430.*
Hauben et al. (Aug. 2001) "Posttraumatic therapeutic vaccination with modified myelin self–antigen prevents complete paralysis while avoiding autoimmune disease." The Journal of Clinical Investigation 108(4): 591–599.*
Cady et al, Response of Murine γō T Cells to the Synthetic Polypeptide Poly–Glu$^{50}$Tyr$^{50}$, J Immunol 165(4):1790–1798 (2000).
Drach et al, "Suppressive effect of synthetic polypeptide GT on the Induction of delayed–type hypersensitivity to a complex GT + methylated bovine serum albumin", Annales D'Immunologie, France 131D(3):299–307 (1980).
Havenith et al, "T Cell Priming In Situ by Intratracheally Instilled Antigen–pulsed Dendritic Cells", Am J Respir Cell Mol Biol 9(5):484–488 (1993).
Lei et al, "Regulation of Immune Responses by I–J Gene Products; III. GT–specific Suppressor Factor is Composed of Separate I–J and Idiotype–bearing Chains", J Immunol 130(3):1274–1279 (1983).
Vidovic et al, "Recessive T Cell Response to Poly (Glu$^{50}$Tyr$^{50}$) Possibly Caused by Self Tolerance", J Immunol 134(6):3563–3568 (1985).

* cited by examiner

Primary Examiner—Elizabeth Kemmerer
Assistant Examiner—Christopher James Nichols
(74) Attorney, Agent, or Firm—Browdy and Neimark, P.L.L.C.

(57) ABSTRACT

Methods and compositions are provided for preventing or inhibiting neuronal degeneration, or for promoting nerve regeneration, in the central nervous system (CNS) or peripheral nervous system (PNS), or for protecting CNS cells from glutamate toxicity, comprising an effective amount of an agent selected from the group consisting of (a) poly-Glu,Tyr and (b) T cells which have been activated by poly-Glue,Tyr.

6 Claims, 3 Drawing Sheets

USE OF POLY-GLU,TYR FOR NEUROPROTECTIVE THERAPY

FIELD OF THE INVENTION

The present invention relates to compositions and methods for the promotion of nerve regeneration or prevention or inhibition of neuronal degeneration to ameliorate the effects of injury or disease of the nervous system (NS). In particular, the invention relates to compositions comprising poly-Glu, Tyr and/or activated T cells treated wite poly-Glu,Tyr, to protect central nervous system (CNS) cells from glutamate toxicity, to promote nerve regeneration or to prevent or inhibit neuronal degeneration caused by injury or disease of nerves within the CNS or peripheral nervous system (PNS) of a human subject. The compositions of the present invention may be administered alone or may be optionally administered in any desired combination.

ABBREVIATIONS

CFA: complete Freund's adjuvant; CNS: central nervous system; MBP: myelin basic protein; NS: nervous system; PBS: phosphate-buffered saline; pEY: Poly-Glu,Tyr; PNS: peripheral nervous system;; Poly-Glu,Tyr: copolymer poly-$Glu^{50}Tyr^{50}$, a random heterocopolymer of L-glutamic acid and L-tyrosine,; RGC: retinal ganglion cells.

BACKGROUND OF THE INVENTION

The nervous system comprises the central (CNS) and the peripheral nervous system (PNS). The CNS is composed of the brain spinal cord and visual system; the PNS consists of all of the other neural elements, namely the nerves and ganglia outside of the brain and spinal cord.

Damage to the nervous system may result from a traumatic injury, such as penetrating trauma or blunt trauma, or a disease or disorder, including but not limited to Alzheimer's disease, Parkinson's disease, Huntington's disease, amyotrophic lateral sclerosis (ALS), diabetic neuropathy, senile dementia, stroke and ischemia.

Maintenance of CNS integrity is a complex "balancing act" in which compromises are struck with the immune system. In most tissues, the immune system plays an essential part in protection, repair, and healing. In the CNS, because of its unique immune privilege, immunological reactions are relatively limited. A growing body of evidence indicates that the failure of the mammalian CNS to achieve functional recovery after injury is a reflection of an ineffective dialog between the damaged tissue and the immune system. For example, the restricted communication between the CNS and blood-borne macrophages affects the capacity of axotomized axons to regrow; transplants of activated macrophages can promote CNS regrowth.

Activated T cells have been shown to enter the CNS parenchyma, irrespective of their antigen specificity, but only T cells capable of reacting with a CNS antigen seem to persist there (Hickey et al, 1991). T cells reactive to antigens of CNS white matter, such as myelin basic protein (MBP), can induce the paralytic disease experimental autoimmune encephalomyelitis (EAE) within several days of their inoculation into naive recipient rats (Ben-Nun, 1981a). Anti-MBP T cells may also be involved in the human disease multiple sclerosis (Ota, K. et al, 1990). However, despite their pathogenic potential, anti-MBP T cell clones are present in the immune systems of healthy subjects (Pette et al, 1990). Activated T cells, which normally patrol the intact CNS, transiently accumulate at sites of central nervous system white matter lesions (Hirschberg et al, 1998).

A catastrophic consequence of CNS injury is that the primary damage is often compounded by the gradual secondary loss of adjacent neurons that apparently were undamaged, or only marginally damaged, by the initial injury (McIntosh, 1993). The primary lesion causes changes in extracellular ion concentrations, elevation of amounts of free radicals, release of neurotransmitters, depletion of growth factors, and local inflammation. These changes trigger a cascade of destructive events in the adjacent neurons that initially escaped the primary injury (Lynch et al, 1994). This secondary damage is mediated by activation of voltage-dependent or agonist-gated channels, ion leaks, activation of calcium-dependent enzymes such as proteases, lipases and nucleases, mitochondrial dysfunction and energy depletion, culminating in neuronal cell death. The widespread loss of neurons beyond the loss caused directly by the primary injury has been called "secondary degeneration."

One of the most common mediators which cause self-propagation of the diseases even when the primary risk factor is removed or attenuated is glutamate, an excitatory amino acid capable of displaying dual activity: playing a pivotal role in normal CNS functioning as an essential neuro-transmitter, but becoming toxic when its physiological levels are exceeded. Elevation of glutamate has been reported in many CNS disorders. In its role as an excitotoxic compound, glutamate is one of the most common mediators of toxicity in acute and chronic (including optic nerve degeneration in glaucoma) degenerative disorders (Pitt et al., 2000). Endogenous glutamate has been attributed to the brain damage occurring acutely after status epilepticus, cerebral ischemia or traumatic brain injury. It may also contribute to chronic neurodegeneration in such disorders as amyotrophic lateral sclerosis and Huntington's chorea.

Intensive research has been devoted to attenuating the cytotoxic effect of glutamate by the use of locally acting drugs, such as N-methyl-D-aspartate (NMDA)-receptor antagonists. Conventional therapy of this type is often unsatisfactory, however, as in neutralizing the toxic effect it is likely to interfere with the physiological functioning. In humans, such compounds have psychotropic and other side effects that make them unsuitable as therapeutic agents. They also have the disadvantage of interfering with the essential physiological functioning of glutamate as a ubiquitous CNS neurotransmitter. Because glutamate activity is essential for normal physiological functioning, yet is potentially devastating after acute injury or in chronic CNS disorders, any attempt to neutralize its harmful effect must do so without eliminating its essential activity at other sites in the body.

Another tragic consequence of CNS injury is that neurons in the mammalian CNS do not undergo spontaneous regeneration following an injury. Thus, a CNS injury causes permanent impairment of motor and sensory functions.

Spinal cord lesions, regardless of the severity of the injury, initially result in a complete functional paralysis known as spinal shock. Some spontaneous recovery from spinal shock may be observed, starting a few days after the injury and tapering off within three to four weeks. The less severe the insult, the better the functional outcome. The extent of recovery is a function of the amount of initially undamaged tissue minus the loss due to secondary degeneration. Recovery from injury would be improved by neuroprotective treatment that could reduce secondary degeneration. For example, alleviation of the effect of glutamate is a frequent target of neuroprotective drug development. Among the drugs which are being developed for this purpose are N-methyl-D-aspartate (NMDA)-receptor or alpha-amino-3-hydroxy-5-methyl-4-isoxazoleproprionic acid (AMPA)-receptor antagonists. These drugs will inevitably have severe side effects as they interfere with the functioning of NMDA and AMPA receptors, which are crucial for normal CNS activity. One of the most intensely studied NMDA-receptor antagonists is MK801, which provides effective neuroprotection but with severe side effects. In animal models of cerebral ischemia and traumatic brain injury, NMDA and AMPA receptor antagonists protect against acute brain damage and delayed behavioral deficits. Such compounds are undergoing testing in humans, but therapeutic efficacy has yet to be established. Other clinical conditions that may respond to drugs acting on glutamatergic transmission include epilepsy, amnesia, anxiety, hyperalgesia and psychosis (Meldrum, 2000).

In the laboratory of the present inventors, it has recently been discovered that activated T cells that recognize an antigen of the NS of the patient confer neuroprotection. Reference is made to U.S. applications Ser. Nos. 09/218,277 and 09/314,161 and PCT Publication WO 99/60021, the entire contents of which is hereby incorporated herein by reference. More specifically, T cells reactive to MBP were shown to be neuroprotective in rat models of partially crushed optic nerve (see also Moalem et al, 1999a) and of spinal cord injury (see also Hauben et al, 2000). Until recently, it had been thought that immune cells do not participate in NS repair. Furthermore, any immune activity in the context of CNS damage was traditionally considered detrimental for recovery. It was quite surprising to discover that NS-specific activated T cells could be used to protect nervous system tissue from secondary degeneration which may follow damage caused by injury or disease of the CNS or PNS. The mechanism of action of such NS-specific T cells has yet to be discovered, but the massive accumulation of exogenously administered T cells at the site of CNS injury suggests that the presence of T cells at the site of injury plays a prominent role in neuroprotection. It appears, however, that the accumulation, though a necessary condition, is not sufficient for the purpose, as T cells specific to the non-self antigen ovalbumin also accumulate at the site, but have no neuroprotective effect (Hirschberg et al, 1998).

In addition to the NS-specific activated T cells, the above-referenced US applications and PCT publication WO 99/60021 disclose that therapy for amelioration of effects of injury or disease of NS can be carried out also with a natural or synthetic NS-specific antigen such as MAG, S-100, β-amyloid, Thy-1, P0, P2, a neurotransmitter receptor, and preferably human MBP, human proteolipid protein (PLP), and human oligodendrocyte glycoprotein (MOG), or with a peptide derived from an NS-specific antigen such as a peptide comprising amino acids 51–70 of MBP or amino acids 35–55 of MOG.

More recently, it has been discovered in the laboratory of the present inventors that a high molecular weight synthetic basic random copolymer consisting of L-Ala, L-Glu, L-Lys and L-Tyr residues with an average molar fraction of 0.141, 0.427, 0.095 and 0.338, designated Copolymer 1 or Cop 1 and being the active ingredient of COPAXONE® (Teva Pharmaceuticals Ltd., Israel), a medicament for the treatment of multiple sclerosis, is able to prevent or inhibit neuronal degeneration, or to promote nerve regeneration, in the CNS or PNS, as well as to protect CNS cells from glutamate toxicity. Reference is made to copending U.S. applications Ser. Nos. 09/487,793, 09/620,216, and 09/765,644, the entire contents of which is hereby incorporated herein by reference. More specifically, Cop 1-specific activated T cells were shown to accumulate in both injured and non-injured neuronal tissues and to be protective in the injured optic nerve against the destructive effect of secondary degeneration, and immunization with Cop 1 was shown to protect against glutamate toxicity.

Oral administration of autoantigen in order to obtain "oral tolerance" has been disclosed for the treatment of various autoimmune diseases. For example, EP 359 783 discloses the oral administration of MBP for the treatment of multiple sclerosis. PCT International Publications WO 91/12816, WO 91/08760 and WO 92/06704 all disclose the treatment of other autoimmune diseases using the oral tolerance method with a variety of autoantigens. Treatment of multiple sclerosis by ingestion or inhalation of Copolymer 1, to achieve suppression of the autoimmune T cell response to myelin antigens, has been disclosed in PCT publication WO 98/30227.

The copolymer poly-Glu$^{50}$Tyr$^{50}$, formerly often termed polyGT and hereinafter called pEY, is a random heterocopolymer of L-glutamic acid and L-tyrosine, with an average length of 100 amino acids and a capacity to elicit strong immune response in certain mouse strains (Vidovic et al., 1985; Vidovic and Matzinger, 1988)). More than 20 years ago it was shown that several inbred as well as congenic resistant strains of mice, which fail to respond to pYE, were shown to develop specific plaque-forming cell (PFC) responses when stimulated by YE complexed to an immunogenic carrier such as methylated bovine serum albumin (MBSA), and that pre-immunization with pEY has a tolerogenic effect on the response to YE-MBSA in some mouse strains and this tolerance can be transferred to normal, syngeneic recipients by spleen cells or thymocytes of EY-primed animals (Debre et al., 1975). None of these publications relates, or suggests, the use of pYE for neuroprotection.

Citation or identification of any reference in this section or any other part of this application shall not be construed as an admission that such reference is available as prior art to the invention.

SUMMARY OF THE INVENTION

It has now been found by the present inventors that pYE and pYE-activated T cells can protect nerve cells from glutamate toxicity and from undergoing secondary degeneration following spinal cord contusion. We examined the spontaneous appearance of T-cells specific to MBP and T-cells specific to EY in rats after spinal cord contusion. In addition, we used active immunization with pEY to attenuate neuronal degeneration induced by glutamate toxicity or by mechanical injury to the spinal cord.

The present invention thus relates to a method for preventing or inhibiting neuronal degeneration, or for promoting nerve regeneration, in the CNS or PNS, or for protecting CNS cells from glutamate toxicity, which comprises administering to an individual in need thereof an effective amount of an agent selected from the group consisting of (a) poly-Glu,Tyr and (b) T cells which have been activated by poly-Glu,Tyr.

The present invention further provides pharmaceutical compositions comprising a therapeutically effective amount of poly-Glu,Tyr-specific activated T cells and methods for using such compositions to promote nerve regeneration or to prevent or inhibit neuronal degeneration in the CNS or PNS, or for protecting CNS cells from glutamate toxicity, in an amount which is effective to ameliorate the effects of an injury or disease of the NS.

As used herein, the term "neuroprotection" refers to the prevention or inhibition of degenerative effects of injury or disease in the NS, including protection from the secondary neurodegenerative effects which persist even when the primary risk factor is removed or attenuated. This includes protection of both white matter and gray matter.

"Activated T cell" as used herein includes (i) T cells that have been activated by exposure to poly-Glu,Tyr and (ii) progeny of such activated T cells.

"Poly-Glu,Tyr-specific activated T cells" as used herein refers to activated T cells having specificity for poly-Glu, Tyr.

The poly-Glu,Tyr-specific activated T cells are used to promote nerve regeneration or to prevent or inhibit the secondary degenerative effects which may follow primary NS injury or the effects of neurodegenerative processes caused by a disease or condition as described hereinafter such as, but not limited to, glaucoma, stroke, ischemia, gunshot, and cerebral damage caused by dangerous sports.

The poly-Glu,Tyr-specific activated T cells serve not only to provide neuroprotection against primary and secondary risk factors associated with myelin (white matter) but also against primary and secondary risk factors associated with the neuronal cell bodies themselves (gray matter) in view of the discovered protection against glutamate toxicity. Thus poly-Glu,Tyr-specific activated T cells are expected to be useful for the purpose of the present invention.

Furthermore, as poly-Glu,Tyr protects from glutamate toxicity, it must also have a regulatory activity, such as by creating regulatory cells or regulatory substances. In view of this regulatory activity, the poly-Glu,Tyr vaccination and the poly-Glu,Tyr-specific activated T cells are expected also to protect white matter and gray matter from damage caused by oxidative stress and other sources of damage to neural cells. In addition, because of this regulatory activity, the present invention can also be used to protect neural cells from autoimmune diseases.

The present invention also provides pharmaceutical compositions comprising a therapeutically effective amount of poly-Glu,Tyr and methods of use of such compositions to promote nerve regeneration or to prevent or inhibit neuronal degeneration in the CNS or PNS, in which the amount is effective to activate T cells in vivo or in vitro, wherein the activated T cells inhibit or ameliorate the effects of an injury or disease of the NS.

In the practice of the invention, therapy for amelioration and treatment of effects of injury or disease comprising administration of poly-Glu,Tyr-specific activated T cells may optionally be in combination with poly-Glu,Tyr.

Additionally, oral administration of poly-Glu,Tyr is effective for neuroprotection after priming with poly-Glu, Tyr administered in adjuvant. Thus, oral poly-Glu,Tyr can be used to boost the activity of the T cells, subsequent to primary activation of such poly-Glu,Tyr, preferably in adjuvant, to build up a critical T cell response immediately after injury.

In another embodiment, cell banks can be established to store poly-Glu,Tyr-sensitized T cells for neuroprotective treatment of individuals at a later time, as needed. In this case, autologous T cells may be obtained from an individual. Alternatively, allogeneic or semi-allogeneic T cells may be stored such that a bank of T cells of each of the most common MHC-class II types are present. In case an individual is to be treated for an injury, preferably autologous stored T cells are used, but, if autologous T cells are not available, then cells should be used which share an MHC type II molecule with the patient, and these would be expected to be operable in that individual. The cells are preferably stored in an activated state after exposure to poly-Glu,Tyr. However, the cells may also be stored in a resting state and activated once they are thawed and prepared for use. The cell lines of the bank are preferably cryopreserved. The cell lines are prepared in any way which is well known in the art. Once the cells are thawed, they are preferably cultured prior to injection in order to eliminate non-viable cells. During this culturing, the cells can be activated or reactivated using the poly-Glu,Tyr, antigen as used in the original activation. Alternatively, activation may be achieved by culturing in the presence of a mitogen, such as phytohemagglutinin (PHA) or concanavalin A (preferably the former). This will place the cells into an even higher state of activation. The few days that it takes to culture the cells should not be detrimental to the patient as the treatment in accordance with the present invention may occur any time up to a week or more after the injury in order to still be effective. Alternatively, if time is of the essence, the stored cells may be administered immediately after thawing.

Figure 1:
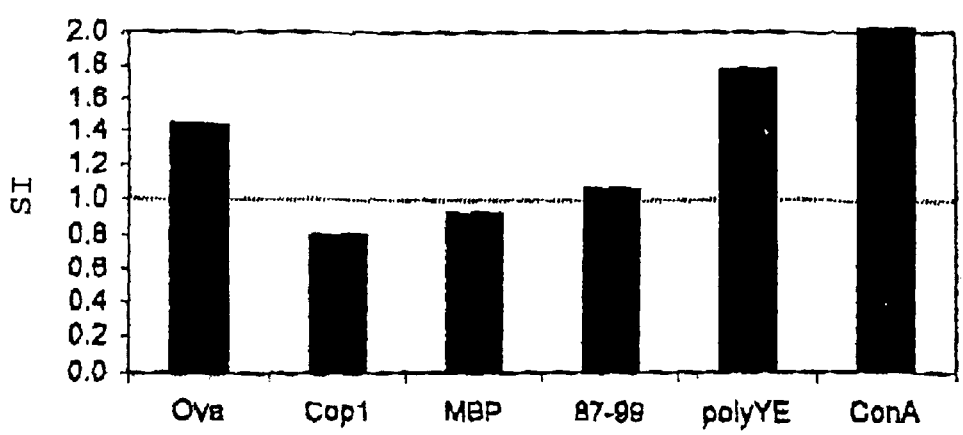
FIG. 1 is a graph showing the results of proliferation assay of splenocytes in response to different antigens: ovalbumin (Ova), copolymer 1(Cop 1), myelin basic protein (MBP), the MBP peptide p87-99, poly-Glu,Tyr (polyYE) and concanavalin A (Con A). The assay was carried out in splenocytes isolated from SPD rats 8–10 days after the rats were subjected to spinal cord contusion. The index was determined in comparison to proliferation of splenocytes in medium not containing any antigen (SI=1).

DETAILED DESCRIPTION OF THE INVENTION (1) Poly-Glu,Tyr Specific Activated T Cells Poly-Glu,Tyr-specific activated T cells are T cells which have been activated in the presence of Poly-Glu,Tyr, as described hereinabove. Such activated T cells of the invention can be used for treating, i.e., ameliorating or inhibiting, the effects of injury or disease of the CNS or PNS that result in NS degeneration or for promoting regeneration in the NS, in particular the CNS. In addition, as glutamate is a mediator in all neurodegenerative diseases, whether chronic or acute, it is intended that such T cells be used for protecting CNS cells from glutamate toxicity and for treating diseases or conditions caused or exacerbated by glutamate toxicity, such as abnormal intraocular pressure.

The Poly-Glu,Tyr-specific activated T cells are preferably autologous, most preferably of the CD4 and/or CD8 phenotypes, but they may also be allogeneic T cells from related donors, e.g., siblings, parents, children, or HLA-matched or partially matched, semi-allogeneic or fully allogeneic donors.

In addition to the use of autologous T cells isolated from the subject, the present invention also comprehends the use of semi-allogeneic T cells for neuroprotection. These T cells may be prepared as short- or long-term lines and stored by conventional cryopreservation methods for thawing and administration, either immediately or after culturing for 1–3 days, to a subject suffering from injury to the central nervous system and in need of T cell neuroprotection.

The use of semi-allogeneic T cells is based on the fact that T cells can recognize a specific antigen epitope presented by foreign antigen presenting cells (APC), provided that the APC express the MHC molecule, class I or class II, to which the specific responding T cell population is restricted, along with the antigen epitope recognized by the T cells. Thus, a semi-allogeneic population of T cells that can recognize at least one allelic product of the subject's MHC molecules, preferably an HLA-DR or an HLA-DQ or other HLA molecule, and that is specific for a poly-Glu,Tyr epitope, will be able to recognize the antigens cross-reactive with poly-Glu,Tyr in the subject's area of NS damage and produce the needed neuroprotective effect. There is little or no polymorphism in the adhesion molecules, leukocyte migration molecules, and accessory molecules needed for the T cells to migrate to the area of damage, accumulate there, and undergo activation. Thus, the semi-allogeneic T cells will be able to migrate and accumulate at the CNS site in need of neuroprotection and will be activated to produce the desired effect.

It is known that semi-allogeneic T cells will be rejected by the subject's immune system, but that rejection requires about two weeks to develop. Hence, the semi-allogeneic T cells will have the two-week window of opportunity needed to exert neuroprotection. After two weeks, the semi-allogeneic T cells will be rejected from the body of the subject, but that rejection is advantageous to the subject because it will rid the subject of the foreign T cells and prevent any untoward consequences of the activated T cells. The semi-allogeneic T cells thus provide an important safety factor and are a preferred embodiment.

It is known that a relatively small number of HLA class II molecules are shared by most individuals in a population. For example, about 50% of the Jewish population express the HLA-DR5 gene. Thus, a bank of specific T cells reactive to poly-Glu,Tyr epitopes that are restricted to HLA-DR5 would be useful in 50% of that population. The entire population can be covered essentially by a small number of additional T cell lines restricted to a few other prevalent HLA molecules, such as DR1, DR4, DR2, etc. Thus, a functional bank of uniform T cell lines can be prepared and stored for immediate use in almost any individual in a given population. Such a bank of T cells would overcome any technical problems in obtaining a sufficient number of specific T cells from the subject in need of neuroprotection during the open window of treatment opportunity. The semi-allogeneic T cells will be safely rejected after accomplishing their role of neuroprotection. This aspect of the invention does not contradict, and is in addition to the use of autologous T cells as described herein.

The poly-Glu,Tyr-specific activated T cells are preferably non-attenuated, although attenuated poly-Glu,Tyr-specific activated T cells may be used. T cells may be attenuated using methods well known in the art, including but not limited to, by gamma-irradiation, e.g., 1.5–10.0 Rads (Ben-Nun et al, 1982); and/or by pressure treatment, for example as described in U.S. Pat. No. 4,996,194 (Cohen et al). In a preferred embodiment the poly-Glu,Tyr-specific activated T cells are isolated as described below. T cells can be isolated and purified according to methods known in the art (Mor et al, 1995). For an illustrative example, see Example 3.2.

Circulating T cells of a subject which recognize poly-Glu,Tyr are isolated and expanded using known procedures. In order to obtain poly-Glu,Tyr-specific activated T cells, T cells are isolated and the poly-Glu,Tyr-specific activated T cells are then expanded by a known procedure (see, for example, Pette et al, 1990, which is incorporated herein by reference in its entirety).

During ex vivo activation, the T cells may be activated by culturing them in medium to which at least one suitable growth promoting factor has been added. Growth promoting factors suitable for this purpose include, without limitation, cytokines, for instance tumor necrosis factor a (TNF-$\alpha$), interleukin-2 (IL-2), and interleukin-4 (IL-4).

In one embodiment, the activated T cells endogenously produce a substance that ameliorates the effects of injury or disease in the NS.

In another embodiment, the activated T cells endogenously produce a substance that stimulates other cells, including, but not limited to, transforming growth factor-$\beta$ (TGF-$\beta$), nerve growth factor (NGF), neurotrophic factor 3 (NT-3), neurotrophic factor 4/5 (NT-4/5), brain derived neurotrophic factor (BDNF); interferon-$\gamma$(IFN-$\gamma$), and interleukin-6 (IL-6), wherein the other cells, directly or indirectly, ameliorate the effects of injury or disease.

Following their proliferation in vitro, the T cells are administered to a mammalian subject. In a preferred embodiment, the T cells are administered to a human subject. T cell expansion is preferably performed using poly-Glu,Tyr.

Poly-Glu,Tyr-activated T cells can be used immediately or may be preserved for later use, e.g., by cryopreservation as described below. Poly-Glu,Tyr-specific activated T cells may also be obtained using previously cryopreserved T cells, i.e., after thawing the cells, the T cells may be incubated with poly-Glu,Tyr, optimally together with peripheral blood lymphocytes (PBL), to obtain a preparation of poly-Glu,Tyr-specific activated T cells.

As will be evident to those skilled in the art, the T cells can be preserved, e.g., by cryopreservation, either before or after culture. Cryopreservation agents which can be used include but are not limited to dimethyl sulfoxide (DMSO), glycerol, polyvinylpyrrolidone, polyethylene glycol, albumin, dextran, sucrose, ethylene glycol, i-erythritol, D-ribitol, D-mannitol, D-sorbitol, i-inositol, D-lactose, choline chloride, amino acids, methanol, acetamide, glycerol monoacetate, inorganic salts, and DMSO combined with hydroxyethyl starch and human serum albumin.

A controlled cooling rate is critical. Different cryoprotective agents and different cell types have different optimal cooling rates. The cooling velocity has an effect on survival of cells and on their transplantation potential. The heat of fusion phase where water turns to ice should be minimal. The cooling procedure can be carried out by use of, e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve.

After thorough freezing, cells can be rapidly transferred to a long-term cryogenic storage vessel. In one embodiment, samples can be cryogenically stored in mechanical freezers, such as freezers that maintain a temperature of about $-8°$ C. or about $-20°$ C. In a preferred embodiment, samples can be cryogenically stored in liquid nitrogen ($-196°$ C.) or its vapor. Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum.

Other methods of cryopreservation of viable cells, or modifications thereof, are available and envisioned for use, e.g., cold metal-mirror techniques.

Frozen cells are preferably thawed quickly (e.g., in a water bath maintained at 37–47° C.) and chilled immediately upon thawing. It may be desirable to treat the cells in order to prevent cellular clumping upon thawing. To prevent clumping, various procedures can be used, including but not limited to the addition before or after freezing of DNAse, low molecular weight dextran and citrate, citrate, hydroxyethyl starch, or acid citrate dextrose.

The cryoprotective agent, if toxic in humans, should be removed prior to therapeutic use of the thawed T cells. One way in which to remove the cryoprotective agent is by dilution to an insignificant concentration.

Once frozen T cells have been thawed and recovered, they are used to promote neuronal regeneration as described herein with respect to non-frozen T cells. Once thawed, the T cells may be used immediately, assuming that they were activated prior to freezing. Preferably, however, the thawed cells are cultured before injection to the patient in order to eliminate non-viable cells. Furthermore, in the course of this culturing over a period of about one to three days, an appropriate activating agent can be added so as to activate the cells, if the frozen cells were resting T cells, or to help the cells achieve a higher rate of activation if they were activated prior to freezing. Usually, time is available to allow such a culturing step prior to administration as the T cells may be administered as long as a week after injury, and possibly longer, and still maintain their neuroregenerative and neuroprotective effect.

The compositions of the invention comprising poly-Glu,Tyr or poly-Glu,Tyr-activated T cells may be used to promote nerve regeneration or to prevent or inhibit secondary degeneration which may otherwise follow primary NS injury, e.g., closed head injuries and blunt trauma, such as those caused by participation in dangerous sports, penetrating trauma, such as gunshot wounds, hemorrhagic stroke, ischemic stroke, glaucoma, cerebral ischemia, or damages caused by surgery such as tumor excision. In addition, such compositions may be used to ameliorate the effects of disease that result in a degenerative process, e.g., degeneration occurring in either gray or white matter (or both) as a result of various diseases or disorders, including, without limitation: diabetic neuropathy, senile dementias, Alzheimer's disease, Parkinson's Disease, facial nerve (Bell's) palsy, glaucoma, Huntington's chorea, amyotrophic lateral sclerosis (ALS), status epilepticus, non-arteritic optic neuropathy, intervertebral disc herniation, vitamin deficiency, prion diseases such as Creutzfeldt-Jakob disease, carpal tunnel syndrome, peripheral neuropathies associated with various diseases, including but not limited to, uremia, porphyria, hypoglycemia, Sjorgren Larsson syndrome, acute sensory neuropathy, chronic ataxic neuropathy, biliary cirrhosis, primary amyloidosis, obstructive lung diseases, acromegaly, malabsorption syndromes, polycythemia vera, IgA and IgG gammapathies, complications of various drugs (e.g., metronidazole) and toxins (e.g., alcohol or organophosphates), Charcot-Marie-Tooth disease, ataxia telangectasia, Friedreich's ataxia, amyloid polyneuropathies, adrenomyeloneuropathy, Giant axonal neuropathy, Refsum's disease, Fabry's disease, lipoproteinemia, etc. In light of the findings with respect to the glutamate protective aspect of the present invention, other clinical conditions that may be treated in accordance with the present invention include epilepsy, amnesia, anxiety, hyperalgesia, psychosis, seizures, abnormally elevated intraocular pressure, oxidative stress, and opiate tolerance and dependence. In addition, the glutamate protective aspect of the present invention, i.e., treating injury or disease caused or exacerbated by glutamate toxicity, can include post-operative treatments such as for tumor removal from the CNS and other forms of surgery on the CNS.

In view of the fact that poly-Glu,Tyr immunization has been surprisingly found useful in protecting against glutamate toxicity, it is expected that poly-Glu,Tyr treatment or poly-Glu,Tyr-activated T cell treatment in accordance with the present invention will be effective in the treatment of the above listed conditions not only in a late phase when myelin is being affected, but also in the early stages in which the neurons are being attacked by factors which cause an elevation in glutamate levels to toxic levels. Thus, the present invention is useful for any indication, i.e., chronic or acute neurodegenerat ion, which is caused or exacerbated by an elevation in glutamate levels, including, but not limited to, the early stages of ischemic stroke and Alzheimer's disease.

In a preferred embodiment, the activated T cells or immunization composition comprising poly-Glu,Tyr of the present invention are used to treat diseases or disorders where promotion of nerve regeneration or prevention or inhibition of secondary neural degeneration is indicated. In a preferred embodiment, the compositions of the present invention are administered to a human subject.

In a preferred embodiment, the present invention contemplates the use of poly-Glu,Tyr administered in adjuvants. Oral administration of poly-Glu,Tyr for neuroprotection, if possible, is contemplated always subsequent to primary activation with poly-Glu,Tyr, preferably in adjuvant. Thus, oral poly-Glu,Tyr can be used to boost the activity of the T cells subsequent to primary activation with poly-Glu,Tyr Poly-Glu,Tyr-activated T cells may also be used to ameliorate the degenerative process caused by neoplasms, without using immunotherapy processes. T cells activated with poly-Glu,Tyr will accumulate at the site of neural degeneration and facilitate inhibition of this degeneration.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

The following exemplification of carriers, modes of administration, and dosage forms are listed as known possibilities from which the carriers, modes of administration, and dosage forms may be selected for use with the present invention. Those of ordinary skill in the art will understand, however, that any given formulation and mode of administration selected should first be tested to determine that it achieves the desired results. Thus, for example, when the active principle is poly-Glu,Tyr, the particular formulation and mode of administration must permit the active principle to act as a vaccine so as to raise T cells activated thereagainat in vivo. If such an immune response is not obtained, then that particular formulation and mode of administration should not be used in accordance with the present invention.

Similarly, if the active principle is activated T cells, then the particular formulation and mode of administration should be tested to ensure that the active T cells being administered reach the bloodstream in an active state so that they can play their protective role in accordance with the present invention.

The term "carrier" refers to a diluent, adjuvant, excipient, or vehicle with which the therapeutic is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin;

and/or a flavoring agent, such as peppermint, methyl salicylate, or orange flavoring.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The compositions may also be formulated in rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

In a preferred embodiment, compositions comprising poly-Glu,Tyr or poly-Glu,Tyr-activated T cells are formulated in accordance with routine procedures as pharmaceutical compositions adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together. Where the composition is to be administered by infusion, it can be dispensed with an infusion bottle containing sterile pharmaceutical grade water or saline. Where the composition is administered by injection, an ampoule of sterile water or saline for injection can be provided so that the ingredients may be mixed prior to administration.

Pharmaceutical compositions comprising poly-Glu,Tyr may optionally be administered with an adjuvant in the usual manner for immunization. Non-limiting examples of such adjuvants include alum and incomplete Freund's adjuvant. Metabolizable lipid emulsions, such as Intralipid or Lipofundin may also be used as vehicles for the poly-Glu,Tyr therapy in the manner disclosed in WO 97/02016, the entire contents of which being hereby incorporated herein by reference. While these materials are known to cause a TH1 to TH2 cytokine shift, there is no reason to believe that TH2 cytokines will not be operable, and perhaps even preferable, for the purpose of the present invention.

When poly-Glu,Tyr is introduced orally, it may be mixed with other food forms and consumed in solid, semisolid, suspension, or emulsion form; and it may be mixed with pharmaceutically acceptable carriers, including water, suspending agents, emulsifying agents, flavor enhancers, and the like. In one embodiment, the oral composition is enterically-coated. Use of enteric coatings is well known in the art.

Poly-Glu,Tyr may also be administered nasally in certain of the above-mentioned forms by inhalation or nose drops. Furthermore, oral inhalation may be employed to deliver poly-Glu,Tyr to the mucosal linings of the trachea and bronchial passages.

The invention also provides a pharmaceutical pack or kit comprising one or more containers filled with one or more of the ingredients of the pharmaceutical compositions of the invention.

In a preferred embodiment, the pharmaceutical compositions of the invention are administered to a mammal, preferably a human, shortly after injury or detection of a degenerative lesion in the NS. The therapeutic methods of the invention may comprise administration of poly-Glu,Tyr OR poly-Glu,Tyr-activated T cells, or a combination thereof. When using combination therapy, poly-Glu,Tyr may be administered before, concurrently or after administration of poly-Glu,Tyr-activated T cells.

In one embodiment, the compositions of the invention are administered in combination with one or more of the following: (a) mononuclear phagocytes, preferably cultured monocytes (as described in PCT publication No. WO 97/09985, which is incorporated herein by reference in its entirety), that have been stimulated to enhance their capacity to promote neuronal regeneration; (b) a neurotrophic factor such as acidic fibroblast growth factor; and (c) an anti-inflammatory therapeutic substance (i.e., an anti-inflammatory steroid, such as dexamethasone or methylprednisolone, or a non-steroidal anti-inflammatory peptide, such as Thr-Lys-Pro (TKP)).

In another embodiment, mononuclear phagocyte cells according to PCT Publication No. WO 97/09985 and U.S. patent application Ser. No. 09/041,280, filed Mar. 11, 1998, are injected into the site of injury or lesion within the CNS, either concurrently, prior to, or following parenteral administration of poly-Glu,Tyr or poly-Glu,Tyr-activated T cells.

In another embodiment, administration of poly-Glu, Tyr or poly-Glu,Tyr-activated T cells may be administered as a single dose or may be repeated, preferably at 2 week intervals and then at successively longer intervals once a month, once a quarter, once every six months, etc. The course of treatment may last several months, several years or occasionally also through the life-time of the individual, depending on the condition or disease which is being treated. In the case of a CNS injury, the treatment may range between several days to months or even years, until the condition has stabilized and there is no or only a limited risk of development of secondary degeneration. In chronic human disease or Parkinson's disease, the therapeutic treatment in accordance with the invention may be for life.

As will be evident to those skilled in the art, the therapeutic effect depends at times on the condition or disease to be treated, on the individual's age and health condition, on other physical parameters (e.g., gender, weight, etc.) of the individual, as well as on various other factors, e.g., whether the individual is taking other drugs, etc.

The optimal dose of the therapeutic compositions comprising poly-Glu,Tyr-activated T cells of the invention is proportional to the number of nerve fibers affected by NS injury or disease at the site being treated. In a preferred embodiment, the dose ranges from about $5 \times 10^6$ to about $10^7$ cells for treating a lesion affecting about $10^5$ nerve fibers, such as a complete transection of a rat optic nerve, and ranges from about $10^7$ to about $10^8$ cells for treating a lesion affecting about $10^6$–$10^7$ nerve fibers, such as a complete transection of a human optic nerve. As will be evident to those skilled in the art, the dose of T cells can be scaled up or down in proportion to the number of nerve fibers thought to be affected at the lesion or site of injury being treated.

To minimize secondary damage after nerve injury, patients can be treated by administering autologous or semi-allogeneic T lymphocytes sensitized to poly-Glu,Tyr. As the window of opportunity has not yet been precisely defined, therapy should be administered as soon as possible after the primary injury to maximize the chances of success, preferably within about one week.

To bridge the gap between the time required for activation and the time needed for treatment, a bank can be established with personal vaults of autologous T lymphocytes prepared for future use for neuroprotective therapy against secondary degeneration in case of NS injury. T lymphocytes are isolated from the blood and then sensitized to poly-Glu, Tyr. The cells are then frozen and suitably stored under the person's name, identity number, and blood group, in a cell bank until needed.

Additionally, autologous stem cells of the CNS can be processed and stored for potential use by an individual patient in the event of traumatic disorders of the NS such as ischemia or mechanical injury, as well as for treated neurodegenerative conditions such as Alzheimer's disease or Parkinson's disease. Alternatively, semi-allogeneic or allogeneic T cells can be stored frozen in banks for use by any individual who shares one MHC type II molecule with the source of the T cells.

The following examples illustrate certain features of the present invention but are not intended to limit the scope of the present invention.

EXAMPLES

Materials and Methods

Animals. All animals were handled according to the regulations formulated by the Institutional Animal Care and Use Committee (IACUC). Mice of the C57BL/6J strain, aged 8–13 weeks, and adult male SPD rats aged 8–12 weeks were supplied by the Animal Breeding Center of the Weizmann Institute of Science (Rehovot, Israel) and housed in light- and temperature-controlled rooms. The rats were matched for age and size in each experiment. Prior to their use in experiments, animals were anesthetized by intraperitoneal administration of ketamine 80 mg/kg and xylazine 16 mg/kg.

Antigens. MBP from the spinal cords of guinea pigs and ovalbumin (OVA), Poly-Glu,Tyr and Con-A were purchased from Sigma (St. Louis, Mo.). Cop 1 was purchased from Teva Pharmaceuticals (Petah Tikva, Israel). The MBP p87-99 peptide was synthesized at the Weizmann Institute of Science (Rehovot, Israel).

Immunization. Mice or rats were immunized with 100 μg of poly-Glu,Tyr emulsified with an equal volume of CFA containing 0.5 mg/ml *Mycobacterium tuberculosis*. The emulsion (total volume 0.1 ml) was injected subcutaneously at one site in the flank in the mice and in the upper back in the rats. Control mice and rats were injected with PBS in CFA (Difco, Detroit, Mich., USA).

Glutamate injection. The right eye of the anesthetized mouse or rat was punctured with a 27-gauge needle in the upper part of the sclera, and a 10-μl Hamilton syringe with a 30-gauge needle was inserted as far as the vitreal body. Mice were injected with a total volume of 1 μl (200 nmole) of L-glutamate dissolved in saline.

T Cell Lines. T cell lines were generated from draining lymph node cells obtained from Lewis rats immunized with the above antigens (Ben-Nun et al, 1981a). The antigen was dissolved in PBS (1 mg/ml) and emulsified with an equal volume of incomplete Freund's adjuvant (IFA) (Difco Laboratories, Detroit, Mich.) supplemented with 4 mg/ml *Mycobacterium tuberculosis* (Difco). Ten days after the antigen was injected into the rats' hind foot pads in 0.1 ml of the emulsion, the rats were killed and their draining lymph nodes were surgically removed and dissociated. The cells were washed and activated with the antigen (10 μg/ml) in stimulation medium containing Dulbecco's modified Eagle's medium (DMEM) supplemented with L-glutamine (2 mM), 2-mercaptoethanol ($5 \times 10^{-5}$ M), sodium pyruvate (1 mM), penicillin (100 IU/ml), streptomycin (100 μg/ml), non-essential amino acids (1 ml/100 ml), and autologous serum 1% (volume/volume). After incubation for 72 hours at 37° C., 98% relative humidity and 10% $CO_2$, the cells were transferred to propagation medium consisting of DMEM, L-glutamine, 2-mercaptoethanol, sodium pyruvate, non-essential amino acids, and antibiotics in the same concentrations as above, with the addition of 10% fetal calf serum (FCS) (volume/volume) and 10% T-cell growth factor derived from the supernatant of concanavalin A (ConA)-stimulated spleen cells (Gillis et al, 1978). Cells were grown in propagation medium for 4–10 days before being restimulated with their antigen (10 μg/ml) in the presence of irradiated (2000 rad) thymus cells ($10^7$ cells/ml) in stimulation medium. The T cell lines were expanded by repeated stimulation and propagation (Ben-Nun et al, 1982).

Crush Injury of Optic Nerve: (a) The optic nerve was subjected to crush injury. Briefly, rats were deeply anesthetized by intraperitoneal (i.p.) injection of Rompun (xylazine, 10 mg/kg; Vitamed, Israel) and Vetalar (ketamine, 50 mg/kg; Fort Dodge Laboratories, Fort Dodge, Iowa). Using a binocular operating microscope, lateral canthotomy was performed in the right eye, and the conjunctiva was incised lateral to the cornea. After separation of the retractor bulbi muscles, the optic nerve was exposed intraorbitally by blunt dissection. Using calibrated cross-action forceps, the optic nerve was subjected to a crush injury 1–2 mm from the eye. Mild and severe crush injuries were inflicted for short-term trials (two weeks), as this time period was shown to be optimal for demonstrating secondary degeneration and its response to treatment (Yoles, 1998). The uninjured contralateral nerve was left undisturbed; (b) Mice or rats were anesthetized and subjected to graded crush injury in the intraorbital portion of the optic nerve, 1–2 mm from the eyeball. With the aid of a binocular operating microscope, the conjunctiva was incised and the optic nerve exposed. Using cross-action calibrated forceps and taking special care not to interfere with the blood supply, the nerve was crushed for 2 s (mice) or 30 s (rats).

Measurement of Secondary Degeneration in the Rat following Optic Nerve Crush, by Retrograde Labeling of RGCs. Secondary degeneration of the optic nerve axons and their attached RGCs was measured by post-injury application of the fluorescent lipophilic dye, 4-(4-(didecylamino) styryl)-N-methylpyridinium iodide (4-Di-10-Asp) (Molecular Probes Europe BV, Netherlands), distally to the lesion site, two weeks after crush injury. Because only axons that are intact can transport the dye back to their cell bodies, application of the dye distally to the lesion site after two weeks ensures that only axons that survived both the primary damage and the secondary degeneration will be counted. This approach enabled differentiation between neurons that are still functionally intact and neurons in which the axons are injured but the cell bodies are still viable, because only those neurons whose fibers are morphologically intact can take up dye applied distally to the site of injury and transport it to their cell bodies. Using this method, the number of labeled RGCs reliably reflects the number of still-functioning neurons. Labeling and measurement were carried out as follows: the right optic nerve was exposed for the second time, again without damaging the retinal blood supply. Complete axotomy was performed 1–2 mm from the distal border of the injury site and solid crystals (0.2–0.4 mm diameter) of 4-Di-10-Asp were deposited at the site of the newly formed axotomy. Five days after dye application the rats were killed. The retina was detached from the eye, prepared as a flattened whole mount in 4% paraformaldehyde solution, and examined for labeled RGCs by fluorescence microscopy.

Labeling of retinal ganglion cells in mice. RCGs were labeled 72 hours before the end of the experiment. Mice were anesthetized and placed in a stereotactic device. The skull was exposed and kept dry and clean. The bregma was identified and marked. The designated point of injection was at a depth of 2 mm from the brain surface, 2.92 mm behind the bregma in the anteroposterior axis and 0.5 mm lateral to the midline. A window was drilled in the scalp above the designated coordinates in the right and left hemispheres. The neurotracer dye FluoroGold (5% solution in saline; Fluorochrome, Denver, Colo.) was then applied (1 µl, at a rate of 0.5 µl/min in each hemisphere) using a Hamilton syringe, and the skin over the wound was sutured.

Assessment of RGC survival in mice. Mice were given a lethal dose of pentobarbitone (170 mg/kg). Their eyes were enucleated and the retinas were detached and prepared as flattened whole mounts in paraformaldehyde (4% in PBS). Labeled cells from 4–6 selected fields of identical size (0.7 mm$^2$) were counted. The selected fields were located at approximately the same distance from the optic disk (0.3 mm) to overcome the variation in RGC density as a function of distance from the optic disk. Fields were counted under the fluorescence microscope (magnification ×800) by observers blinded to the treatment received by the mouse. The average number of RGCs per field in each retina was calculated.

Assessment of RGC survival in rats. Survival of RGCs in rats was measured after post-injury application of the fluorescent lipophilic dye, 4-(4-(didecylamino) styryl)-N-methylpyridinium iodide (4-Di-10-Asp) (Molecular Probes Europe BV, Netherlands), distally to the optic nerve head. Labeling and measurement were carried out as follows: the optic nerve was exposed without damaging the retinal blood supply. Complete axotomy was performed 1–2 mm from the optic nerve head and solid crystals (0.2–0.4 mm diameter) of 4-Di-10-Asp were deposited at the site of the formed axotomy. Five days after dye application the rats were killed. The retina was detached from the eye, prepared as a flattened whole mount in 4% paraformaldehyde solution, and examined for labeled RGCs by fluorescence microscopy. In the IOP experimental animals, the ganglion cells were labeled by retrograde transport dextran tetramethylrhodamine (DTMR) (Molecular Probes, OR). Crystals of 3000 MW DTMR were applied to the cut end of the optic nerve about 2 to 3 mm from the globe. Twenty-four hours later the retinas were whole-mounted and labeled ganglion cells in 8 regions, 2 in each quadrant, (0.66 to 1.103 mm from the edge of the optic disk) were counted with 400× magnification.

Histological analysis. Seven days after glutamate or saline injection the mice were killed by injection of a lethal dose of pentobarbitone (170 mg/kg) and their eyes were removed and fixed in formaldehyde (4% in PBS) for 48 h at 4° C. Sections (10 µm thick) were embedded in paraffin and stained with hematoxylin and eosin (H&E).

Generation of ocular hypertension in rats/Elevation of intraocular pressure in rats. Male Lewis rats were anesthetized with a mixture of ketamine (15 mg/kg), acepromazine (1.5 mg/kg), and xylazine (0.3 mg/kg). An increase in intraocular pressure (IOP) was achieved by laser photocoagulation of the limbal and episcleral veins. Rats received 2 laser treatments, 1 week apart, with a blue-green argon laser (1 watt for 0.2 s, delivering a total of 130–150 spots of 50 µm in the 2 treatments; Coherent, Palo Alto, Calif.). IOP was measured once a week using TONO-PEN (Mentor, Norwell, Mass.), after injecting the rats intramuscularly with the veterinary tranquilizer acepromazine 3.0 mg/kg and applying proparacaine 0.5% topically on the eyes to anesthetize the cornea.

Example 1

Immunization With Poly-Glu,Tyr

SPD rats were anesthetized and their spinal cords were exposed by laminectomy at the level of T8. One hour after induction of anesthesia, a 10-g rod was dropped onto the laminectomized cord from a height of 50 mm, using the NYU impactor (Basso et al., 1995 and 1996).

Rats were killed 8–10 days after spinal cord contusion and their spleens were excised and pressed trough a fine wire mesh. The washed cells (2×10$^6$/ml) were cultured in triplicate in flat-bottomed microtiter wells in 0.2 ml proliferation medium containing DMEM supplemented with L-glutamine (2 mM), 2-mercaptoethanol (5×10$^{-5}$ M), sodium pyruvate (1 mM), penicillin (100 IU/ml), streptomycin (100 µg/ml), non-essential amino acids, and autologous rat serum 1% (vol/vol) with the antigen (15 µg/ml) or Con A (1.25 µg/ml), and irradiated thymocytes (2000 rad, 2×10$^6$ cells/ml). The proliferative response to different antigens namely Ova, Cop 1, MBP, 87-99, poly-Glu,Tyr and Con A, was determined by measuring the incorporation of [$^3$H]thymidine (1 µCi/well), which was added for the last 16 h of a 72 h culture. The splenocyte proliferation index (SI) was determined as compared to the proliferation of the splenocytes in medium with no antigen. (SI=1 indicates no proliferation response to the antigen above the proliferation without any antigen). This parameter is indicative of the physiological T-cell repertoire in contused animals. Con-A is the positive control. The results in FIG. 1 indicate that in the spinally contused rats there is a high occurrence of poly-Glu,Tyr (polyYE) T-cells, more than Cop-1 or MBP T-cells.

Example 2

Protection of Optic Nerve Fibers from Glutamate Toxicity

In order to find out whether poly-Glu,Tyr can impart a more general neuroprotection from hostile environmental conditions caused by glutamate-induced toxicity, the following experiment was conducted.

Injection of the excitatory neurotransmitter glutamate into the vitreal body of C57Bl/6J mice eye causes dose-dependent death of the cell bodies of optic nerve neurons. A previous study showed that the onset of RGC death is delayed (by more than 24 hours after glutamate injection) and is apoptotic-like.

In the present experiment, 8-week-old male C57Bl/6J mice were immunized subcutaneusly with 100 µg poly-Glu, Tyr emulsified in CFA, 7 days prior to glutamate injection. A group of mice immunized at the same time with PBS emulsified in CFA to rule out a non-specific effect of the immunization and a group of non-immunized mice served as controls. Mice in all three groups received an injection of glutamate (400 nmole) into the vitreous of the right eye. The left eye received no injection and was used as an intact control. Seven days after glutamate injection, the eyes were excised and RGC survival was determined.

The average number of RGCs per $mm^2$ counted in the intact retinas of the poly-Glu,Tyr-immunized, the PBS-immunized, and the non-immunized mice were 2796±165, 2874±197 and 2807±42, respectively, indicating that immunization had no effect on survival of RGCs in the contralateral intact eye. These average values of RGCs per $mm^2$ in intact retina in all 3 experimental groups were therefore combined and taken as 100% RGC survival (0% toxicity).

Figure 2:
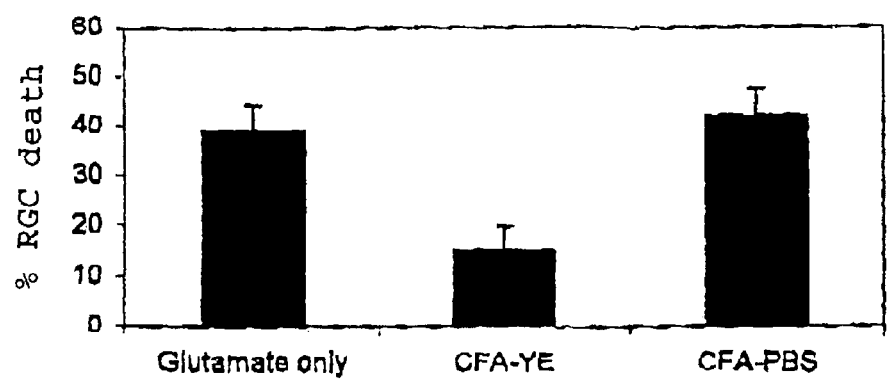
FIG. 2 is a graph showing how immunization with polyYE attenuates significantly retinal ganglion cells (RGCs) death induced by glutamate. The number of labeled (surviving) $RGC/mm^2$ in retinas excised from C57BL/6J mice who had been immunized with an emulsion of polyYE in complete Freund's adjuvant (CFA-YE) or with PBS in CFA (CFA-PBS,), 7 days prior to intravitreal glutamate injection, and 7 days later was counted. Bars represent mean±sem of percentage of RGC death compared to the naïve retina.

The results depicted in FIG. 2 show that immunization of the mice with poly-Glu,Tyr in CFA (CFA-YE) significantly attenuated the glutamate-induced RGC death compared to immunization with PBS (t-test, p=0.007) or to non-immunization (t-test, p=0.01). There was no difference in RGC survival between the 2 latter groups (t-test, p=0.71).

Example 3

Neuroprotection In Spinal Cord Injury

Acute incomplete spinal cord injury at the low thoracic levels causes an immediate loss of hindlimb motor activity that spontaneously recovers within the first 12 days post-injury and stabilizeS on deficient movement abilities. The amount of motor function restoration is the sum up effect of the positive recovery from spinal shock and the negative effect of longitudinal and ventral spread of damage. A therapeutic approach aiming at reducing the spread of damage through neuroprotection will result in a better recovery in terms of hindlimb motor activity.

In the following experiments, the effect of active or passive immunization with poly-Glu,Tyr on motor activity of the hindlimb after spinal cord contusion, was tested.

3.1 Active Immunization With Poly-Glu,Tyr : The Effect Of pYE/CFA Immunization On Rat Recovery From Spinal Cord Contusion A contusive injury of the spinal cord was inflicted on anesthetized 12 SPD male rats by using the NYU impactor device to drop a 10-g rod from a height of 50 mm onto the exposed laminectomized spinal cord at level T8. The NYU impactor device used allowed, for each animal, measurement of the trajectory of the rod and its contact with the exposed spinal cord to allow uniform lesion.

Due to the spinal shock, the motor skills of the rats' hindlimbs initially disappeared, but recovered with time to reach a steady state of deficient motor activity. The amount of this deficiency caused by the injury can be reduced with adequate neuroprotective treatment.

Figure 3:
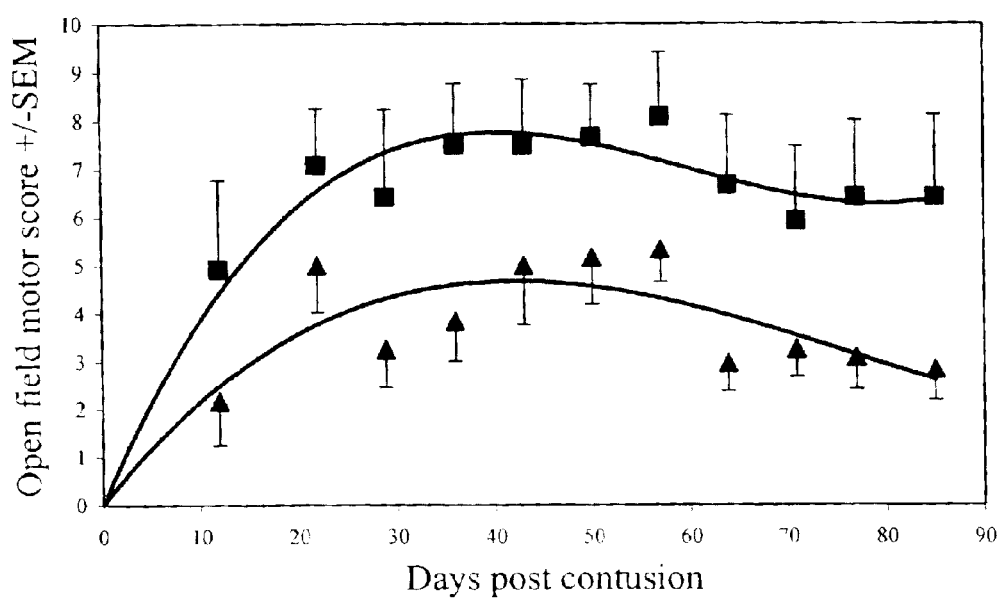
FIG. 3 depicts the effects of pYE/CFA immunization on the recovery of rats from spinal cord contusion. The graph presents the mean±sd of hindlimbs motor activity scores in open field (BBB test as described in Example 3.1 hereinafter) with time after spinal cord injury in two groups of SPD rats immunized with pYE/CFA (squares) or CFA-PBS (control; triangles) immediately after spinal cord injury.

The rats were divided into 2 groups (6 each) according to their impact errors to achieve similar groups. One group of rats were SC immunized in their upper back with PBS/CFA (triangles). The other group were SC immunized with pYE/CFA (100 µg/rat, squares). Both groups were immunized immediately after the injury and 7 days later both groups received a second immunization identical to the first one. poly-Glu,Tyr ( ) or PBS emulsified with CFA. The hindlimb motor skills of the animals were scored using a scoring method developed by Basso et al., 1995 (the locomotor activity is scored (range of 0–21) according to the Basso, Beattie, Bresnahan (BBB) Locomotor Rating Scale) following the kinetics and amount of hindlimb motor activity in the two experimental groups. Approximately twice a week, locomotor activity of the trunk, tail and hind limbs in an open field was evaluated by placing the rat for 4 min in the middle of a circular enclosure made of molded plastic with a smooth, nonslip floor (90 cm diameter, 7 cm wall height). The results depicted in FIG. 3 show that rats treated with pYE (squares) showed a tendency to recover better than PBS-treated rats.

3.2 Passive Immunization With Poly-Glu,Tyr

In order to examine whether poly-Glu,Tyr-specific T cells also provide neuroprotection after spinal cord injury, the following experiment was conducted.

For the preparation of the T cells, four SPD rats were SC immunized in their lower back with pYE/CFA (125 µg/rat). Seven days later their splenocytes were harvested and a single cell suspension was prepared by pressing the spleens against a metal mesh using the plunger of a syringe. The splenocytes were activated in culture for 3 days with pYE 10 µg/ml). The cells were harvested, washed in PBS and counted.

Another group of 12 male SPD rats went trough surgery and their spinal cord contused at T7 level using 10-g weight drop from 50 mm height as described in Example 3.1 above. Immediately after the contusion, the rats were divided to 2 equal groups according to their impact errors. One group received intravenously 0.5 ml of PBS and the other group received splenocytes activated with pYE ($30 \times 10^6$/0.5 ml PBS/rat). The rats were followed for their recovery of function using the open field BBB score.

Figure 4:
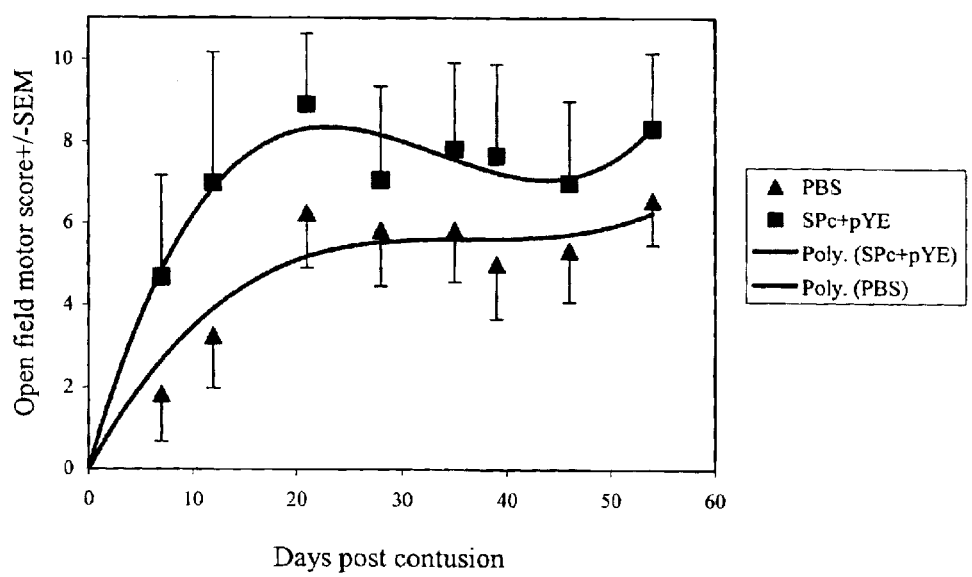
FIG. 4 depicts the effects of adoptive transfer of splenocytes activated with pYE on spinal cord injury recovery. The graph presents the mean±sd of hindlimbs motor activity scores in open field with time after spinal cord injury in two groups of SPD rats injected intraperitoneally with CFA-YE-activated T cells (SPc+pYE; squares) or CFA-PBS-treated T cells (control; triangles) immediately after spinal cord injury.

The results depicted in FIG. 4 show that the rats treated with splenocytes activated with pYE (squares) recovered better than the control group (triangles).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Basso, D M, Beattie, M S and Bresnahan, J C, 1995, "A sensitive and reliable locomotor rating scale for open field testing in rats, *J. Neurotrauma* 12(1):1–21.

Basso D M, Beattie, M S and Bresnahan, J C, 1996, "Graded histological and locomotor outcomes after spinal cord contusion using the NYU weight-drop device versus transection, *Exp.Neurol.* 139(2):244–256.

Ben-Nun et al, "The rapid isolation of clonable antigen-specific T lymphocyte lines capable of mediating autoimmune encephalomyelitis", *Eur. J. Immunol.* 11(3): 195–199 (1981)

Debre et al., "Genetic control of specific immune suppression. II. H-2-linked dominant genetic control of immune suppression by the random copolymer L-glutamic acid50-L-tyrosine50 (GT)",*J. Exp. Med.* 142(6):1447–54 (1975)

Hauben et al, "Autoimmune T cells as potential neuroprotective therapy for spinal cord injury", *Lancet* 355:286–287 (2000)

Hickey, W. F. et al, "T-lymphocyte entry into the central nervous system",*J. Neurosci. Res.* 28(2):254–260 (1991)

Hirschberg et al, "Accumulation of passively transferred primed T cells independently of their antigen specificity following central nervous system trauma" *J. Neuroimmunol.* 89(1–2):88–96 (1998)

Lynch et al, "Secondary mechanisms in neuronal trauma, *Curr. Opin. Neurol.* 7(6):510–516 (1994)

McIntosh, T. K., "Novel pharmacologic therapies in the treatment of experimental traumatic brain injury: a review", *J. Neurotrauma* 10(3):215–261 (1993)

Meldrum, "Glutamate as a neurotransmitter in the brain: review of physiology and pathology", *J. Nutr.* 130: (4S Suppl): 1007S–1015S (2000)

Moalem et al, "Autoimmune T cells protect neurons from secondary degeneration after central nervous system axotomy", *Nat. Med.* 5:49–55 (1999a)

Mor et al, "Pathogenicity of T cells responsive to diverse cryptic epitopes of myelin basic protein in the Lewis rat", *J. Immunol.* 155(7):3693–3699 (1995)

Ota et al, "T-cell recognition of an immunodominant myelin basic protein epitope in multiple sclerosis", *Nature* 346 (6280):183–187 (1990)

Pette et al, "Myelin basic protein-specific T lymphocyte lines from MS patients and healthy individuals", *Proc. Natl. Acad. Sci. USA* 87(2):7968–7972 (1990)

Pitt et al., "Glutamate excitotoxicity in a model of multiple sclerosis", *Nat Med*, 6:67–70 (2000)

Vidovic et al., Recessive T cell response to poly $Glu^{50}Tyr^{50}$) possibly caused by self tolerance", *J. Immunol.* 134(6): 3563–68 (1985)

Vidovic and Matzinger, "Unresponsiveness to a foreign antigen can be caused by self-tolerance", *Nature* 336:222 (1988)

What is claimed is:

1. A method for lessening retinal ganglion cell (RGC) death and/or lessening damage to the optic nerve arising from a condition selected from the group consisting of glaucoma, increased intraocular pressure and glutamate toxicity, comprising:

administering to an individual in need of such treatment an effective amount of poly-Glu,Tyr, thereby lessening RGC death and/or lessening damage to the optic nerve.

2. A method in accordance with claim 1, where said individual in need is one whose damage to the optic nerve is caused or exacerbated by glutamate toxicity.

3. A method in accordance with claim 1, wherein said individual in need is one whose damage to the optic nerve arises from abnormally elevated intraocular pressure.

4. A method in accordance with claim 1, where said individual in need is one whose damage to the optic nerve arises from glaucoma.

5. A method in accordance with claim 1, wherein said administration of an effective amount of poly-Glu,Tyr to said individual in need causes lessening of RGC death.

6. A method in accordance with claim 1, wherein said administration of an effective amount of poly-Glu,Tyr to said individual in need causes both lessening of RGC death and lessening damage to the optic nerve.

* * * * *